United States Patent
McCarthy et al.

(10) Patent No.: US 10,527,566 B2
(45) Date of Patent: Jan. 7, 2020

(54) METHODS FOR DETERMINING OIL AND WATER COMPOSITIONS IN DRILLING MUDS

(71) Applicant: THE REGENTS OF THE UNIVERSITY OF CALIFORNIA, Oakland, CA (US)

(72) Inventors: Michael J. McCarthy, Davis, CA (US); Victor Lim, Pacifica, CA (US); Lu Zhang, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 568 days.

(21) Appl. No.: 15/351,259

(22) Filed: Nov. 14, 2016

(65) Prior Publication Data

US 2017/0122891 A1  May 4, 2017

Related U.S. Application Data

(63) Continuation of application No. PCT/US2015/031165, filed on May 15, 2015.
(Continued)

(51) Int. Cl.
*G01V 3/00* (2006.01)
*G01N 24/08* (2006.01)
(Continued)

(52) U.S. Cl.
CPC ......... *G01N 24/081* (2013.01); *G01R 33/448* (2013.01); *G01R 33/50* (2013.01)

(58) Field of Classification Search
CPC .................................................. G01N 24/081
(Continued)

(56) References Cited

U.S. PATENT DOCUMENTS

| 5,023,551 A | 6/1991 | Kleinberg et al. |
| 6,107,796 A | 8/2000 | Prammer |

(Continued)

OTHER PUBLICATIONS

Kantzas, Apostolos et al., "Applications of Low Field MR Techniques in the Characterization of Oil Sand Mining, Extraction and Upgrading Processes", The Canadian Journal of Chemical Engineering, vol. 83, Feb. 2005, pp. 145-150.
(Continued)

*Primary Examiner* — Louis M Arana
(74) *Attorney, Agent, or Firm* — O'Banion & Ritchey LLP; John P. O'Banion

(57) ABSTRACT

A nuclear magnetic resonance (NMR) system and method for determining oil and water composition in drilling mud by separating out signals from oil and water in a two dimensional relaxation space wherein the oil and water ratio is a function of the separated out signals. The spin-lattice relaxation time distribution or a spin-spin relaxation time distribution of the sample is measured and a spin-lattice versus spin-spin or a spin-spin versus diffusion two-dimensional procedure is applied to separate the components of the drilling fluid. The signal intensities from the oil and water regions of the one-dimensional or two-dimensional NMR measurements are used to quantify the relative portion of the proton NMR signal from the oil and water and to determine the ratio of oil and water in the drilling mud.

20 Claims, 4 Drawing Sheets

Related U.S. Application Data

(60) Provisional application No. 61/993,560, filed on May 15, 2014.

(51) Int. Cl.
  *G01R 33/44* (2006.01)
  *G01R 33/50* (2006.01)

(58) Field of Classification Search
  USPC .......................................... 324/303, 306, 309
  See application file for complete search history.

(56) References Cited

U.S. PATENT DOCUMENTS

| | | | |
|---|---|---|---|
| 6,140,817 | A | 10/2000 | Flaum et al. |
| 6,630,357 | B2 | 10/2003 | Mirotchnik et al. |
| 6,794,864 | B2 | 9/2004 | Mirotchnik et al. |
| 6,859,033 | B2* | 2/2005 | Speier ................ G01V 3/32 324/303 |
| RE40,167 | E | 3/2008 | Edwards et al. |
| 8,248,067 | B2* | 8/2012 | Ong ................... G01F 1/716 324/303 |
| 9,018,950 | B2* | 4/2015 | Li ....................... G01N 24/081 324/309 |
| 10,031,255 | B2* | 7/2018 | Song ................... G01V 3/32 |
| 2004/0041562 | A1 | 3/2004 | Speier |
| 2010/0039109 | A1 | 2/2010 | Cheng et al. |
| 2013/0106413 | A1 | 5/2013 | Hopper et al. |
| 2013/0261979 | A1 | 10/2013 | Al-Muthana et al. |
| 2013/0325408 | A1 | 12/2013 | Song |
| 2018/0372906 | A1* | 12/2018 | Hou ..................... G01V 3/18 |

OTHER PUBLICATIONS

Kantzas, A. et al., "Low Field NMR Applications in Oil Sands Mining and Extraction", International Symposium of the Society of Core Analysts, Toronto, Canada, Aug. 21-25, 2005, pp. 1-12.

Jin, Yuqi et al., Rapid, Accurate Measurement of the Oil and Water Contents of Oil Sludge Using Low-Field NMR, Ind. Eng. Chem. Res. 2013, 52, Jan. 21, 2013, pp. 2228-2233.

Mitchell, J. et al., "A Rapid Measurement of T1/T2: The DECPMG sequence", Journal of Magnetic Resonance, vol. 200, Issue 2, Oct. 2009, pp. 198-206.

Hurlimann, M.D. et al., "Quantitative Measurement of Two-Dimensional Distribution Functions of Diffusion and Relaxation in Grossly Inhomogeneous Fields", Journal of Magnetic Resonance, vol. 157, Issue 1, Jul. 2002, pp. 31-42.

Korean Intellectual Property Office (KIPO), International Search Report and Written Opinion, dated Aug. 26, 2015, related PCT International Application No. PCT/US2015/031165, pp. 1-14, with claims searched, pp. 15-18.

* cited by examiner

METHODS FOR DETERMINING OIL AND WATER COMPOSITIONS IN DRILLING MUDS

CROSS-REFERENCE TO RELATED APPLICATIONS

This application is a 35 U.S.C. § 111(a) continuation of PCT international application number PCT/US2015/031165 filed on May 15, 2015, incorporated herein by reference in its entirety, which claims priority to, and the benefit of, U.S. provisional patent application Ser. No. 61/993,560 filed on May 15, 2014, incorporated herein by reference in its entirety. Priority is claimed to each of the foregoing applications.

The above-referenced PCT international application was published as PCT International Publication No. WO 2015/175985 on Nov. 19, 2015, which publication is incorporated herein by reference in its entirety.

STATEMENT REGARDING FEDERALLY SPONSORED RESEARCH OR DEVELOPMENT

Not Applicable.

INCORPORATION-BY-REFERENCE OF COMPUTER PROGRAM APPENDIX

Not Applicable

BACKGROUND

1. Technical Field

The present technology pertains generally to magnetic resonance diagnostic schemes and more particularly to an NMR based method for determining the oil and water composition in drilling mud by separating out signals from oil and water in a two dimensional relaxation space wherein the oil and water ratio is a function of the separated out signals.

2. Background

In the exploration of oil or gas by drilling, a drilling fluid or mud is circulated in the bore hole to cool and lubricate the drill bit, move drill cuttings away from the drill bit and to the surface for removal, maintain the integrity of the wellbore and to create a counterbalance hydrostatic pressure to prevent well blowouts. Circulation of drilling muds to the drill bit and back to the surface can often take several hours to complete.

The drilling fluid may accumulate water from geological formations or from the surface as drilling progresses and the drilling fluid completes its circuit through the wellbore. The water content of the drilling mud composition is monitored, in part, to ensure that the hydrostatic pressure imposed by the drilling mud exceeds the formation pressure of the well.

Drilling fluid is a complex mixture of liquids, solids and additional chemicals. This is most often an emulsion either a water-in-oil or oil-in-water emulsion. The range of components in drilling mud is extremely broad and may include water, oil, soluble salts, viscosity modifiers (e.g., emulsifiers, viscosifiers) and other chemicals and solids that are added to control the physical and chemical properties of the mud. Materials that may be added to drilling fluids include synthetic based oils, diesel fuel, lime, calcium chloride, Bentonite, barite, biocides, and other similar materials. The properties of the drilling mud or fluid are defined by the drilling requirements and the mud engineer makes the decision based on the physical and chemical analysis of the drilling mud as well as from personal knowledge of the drilling operation.

In addition to the purposeful addition of compounds or materials to the mud, there will be drill cuttings that are accumulated in the mud over time as the well is drilled. Drill cuttings are any material that is extracted from the borehole during the drilling operation. Drill cuttings have a wide range of components and could include granite, gypsum, clay, dolomite, chalk, quartz, sand, sulfur, sandstone, shale as well as other minerals, rocks and salts, depending upon the underground formations that are drilled.

The general water and oil volume percent measurement of drilling mud is conventionally performed by using a retort. A set volume of drilling fluid is placed in the retort and the oil and water phases are then distilled off of the sample. The solids remain and the oil and water fractions are collected in a graduated cylinder. The volumes of the oil and water phases are then read directly off of the scale of the graduated cylinder and can be reported as a ratio, a volume percent of water or a volume percent of oil. This measurement procedure is slow and can only be performed on a small volume of the sample of drilling material.

Distillation apparatuses such as retorts are typically used to measure the oil and water compositions in drilling muds, but these devices are time consuming to operate and clean. One NMR relaxometry based approach uses solely $T_2$ measurements. A weakness with $T_2$ measurement techniques is possible overlap of the peaks that are attributed to oil and water. A method to get around this is to "deconvolute" the peak by looking at the second derivative of the peak to determine a cutoff for oil and water. This is problematic as this requires the peak to have a shoulder in order to partition the peak.

A second NMR based method involves adding a paramagnetic ion to the drilling mud which shifts the water signal from the overlapped peak to a shorter relaxation time. This is problematic for solutions where the overlapped peak is already at a very short relaxation time. The added paramagnetic ion shifts the signal from the water in the overlapped peak to a lower relaxation time resulting in a signal that cannot be measured using current detection techniques. However, adding a paramagnetic ion is not practical for in-line and on-line determination of water and oil fractions in a stream of drilling mud.

Accordingly, there is a need for efficient methods and materials for accurately and quickly analyzing drilling muds than is available with existing techniques. There is also a need for materials and methods that provide effective separations at low cost. The presently described technology satisfies these needs as well as others and is generally an improvement over the art.

BRIEF SUMMARY

The technology pertains to a nuclear magnetic resonance (NMR) system and method for determining the oil and water composition in drilling mud by separating out signals from oil and water in a two dimensional relaxation space wherein the oil and water ratio is a function of the separated out signals. An NMR sequence is set up to acquire a two dimensional data set for $T_1$-$T_2$ relaxation measurements and correlation spectra. The sequence must effectively capture $T_1$-$T_2$ data. In one embodiment, the sequence is a saturation recovery sequence followed by a CPMG echo train. The produced data is preferably transformed from a time space to a relaxation component space with a two dimensional inverse Laplace transform or similar alternative transform. Components that are under or over detection limits of the applied sequence are eliminated. The data is then projected to a plane perpendicular to the line corresponding to $T_1/T_2=1$. The projected data form into a $T_1/T_2$ spectrum in that plane.

The acquired spectrum is fitted to Gaussian peaks to determine the peak areas or integrated numerically or fitted with an alternate function that closely approximates the spectrum features. An oil-water cutoff value is determined based on the maximum peak intensity and peak shapes. The areas of the peaks at this cutoff and above are attributed to signal from oil and the peak areas below this cutoff are attributed to water. The areas of peaks for water and oil are then summed, respectively. Hydrogen Indexes may be used to account for the differences in signal intensity from oil and water per unit volume. The oil and water ratio is then determined.

In one embodiment, a nuclear magnetic resonance (NMR) method is provided for determining the oil and water composition in drilling mud, including: (a) collecting a sample of the drilling mud; (b) placing the sample in an NMR compatible vial; (c) placing the sample in an NMR system; (d) measuring the spin-lattice relaxation time distribution of the sample, or the spin-spin relaxation time distribution of the sample; (e) if the distributions of oil and water phases overlap in the drilling fluid, using a two-dimensional procedure such as spin-lattice versus spin-spin, or spin-spin versus diffusion to separate the components of the drilling fluid; (f) integrating the signal intensities from the oil and water regions of the one-dimensional or two-dimensional NMR measurements to quantify the relative portion of the proton NMR signal from the oil and water; and (g) determining the ratio of oil and water from the proton NMR signals.

In another embodiment, a nuclear magnetic resonance method is provided for determining the oil and water composition in drilling mud that has the steps of first establishing an NMR sequence to acquire a two dimensional data set for $T_1$-$T_2$ correlation spectra such as a saturation recovery sequence followed by a Car-Purcell-Meiboom-Gill (CPMG) echo train sequence or Hahn echo sequence. Then the data set is transformed from a time space to a relaxation component space with a two dimensional inverse Laplace transform. Next, components that are under or over the detection limits of the sequences are eliminated and the transformed data is projected to a plane perpendicular to the line corresponding to $T_1/T_2=1$ where the projected data form a $T_1/T_2$ spectrum in that plane. The projected data spectrum is then fitted to Gaussian peaks to determine the peak areas. The maximum peak intensity and shape are used to determine an oil-water cutoff value based on the maximum peak intensity. The areas of peaks located at the cutoff value and above are attributed to a signal from oil; and the areas of peaks below the cutoff value are attributed to water. The peak areas for water and for oil are then summed, respectively. Differences in signal intensity from oil and water may be accounted for by using Hydrogen Indexes to account for the differences. Then, observed differences in signal intensity are used to determine an oil and water ratio.

According to one aspect of the technology, a noninvasive nondestructive nuclear magnetic resonance based analysis of a sample of drilling fluid is provided based on the inherent differences in the spin-spin lattice relaxation times, the spin-lattice relaxation times and the self-diffusion coefficients of the oil and water phases.

Another aspect of the described technology is to provide a system and method that can provide very quick analysis of oil and water ratios of drilling mud within an actively pumped pipeline contained in a nuclear magnetic resonance spectrometer magnet and radio frequency coil. The flow is stopped and the 1-D or 2-D nuclear magnetic resonance procedure is applied to measure the oil and water volume percent of the fluid.

Further objects and aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawing which is for illustrative purposes only.

DETAILED DESCRIPTION

Referring more specifically to the drawings, for illustrative purposes, embodiments of the apparatus and methods for determining the oil and water composition of drilling muds are generally shown. Embodiments of the technology are described generally in FIG. 1A to FIG. 2B to illustrate the methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Generally, the oil-water ratio of a sample of drilling mud can be identified with NMR by measuring the spin-lattice relaxation time distribution of the sample, or the spin-spin relaxation time distribution of the sample. If the distributions of oil and water phases overlap in the drilling fluid, then a two-dimensional correlation procedure such as spin-lattice versus spin-spin, or spin-spin versus diffusion to separate the components of the drilling fluid can be used. Then the signal intensities from the oil and water regions of the one-dimensional or two-dimensional NMR measurements can be used to quantify the relative portion of the proton NMR signal from the oil and water and the ratio of oil and water from the proton NMR signals from the mud can be determined.

Figure 1A:
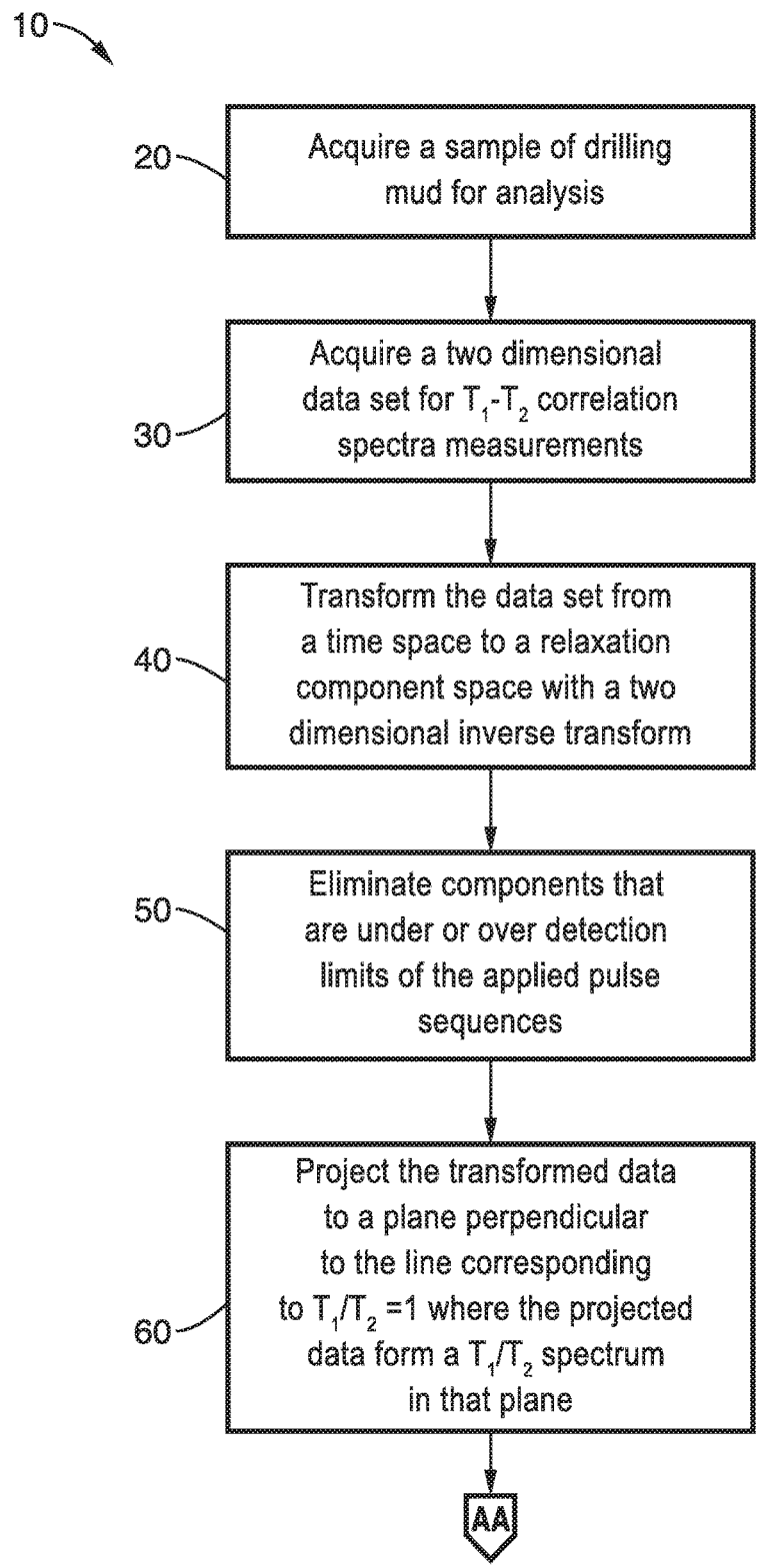
FIG. 1A-FIG. 1B depict a schematic flow diagram of a method of estimating oil-water ratios using NMR signals separated out into two-dimensional relaxation space according to one embodiment of the technology.
Figure 1B:
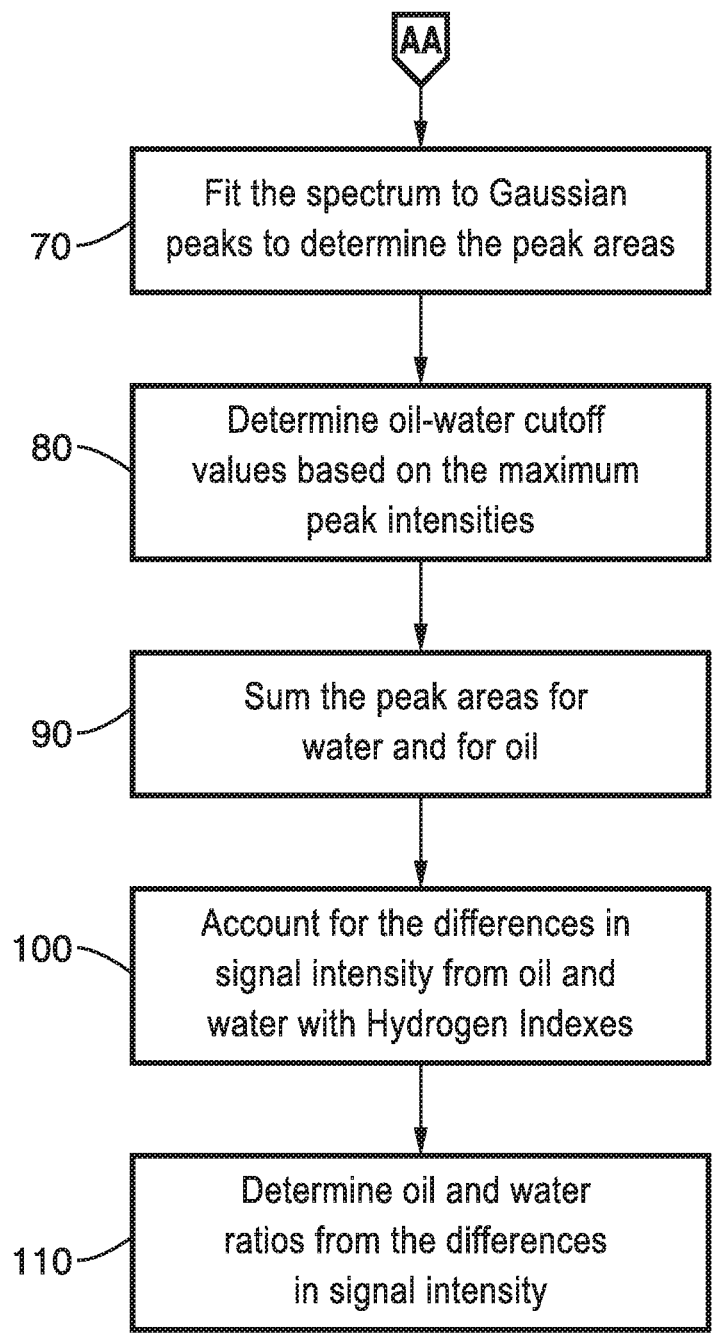

Turning now to FIG. 1A and FIG. 1B, one method 10 for NMR analysis of drilling muds from a sample of a stream of drilling mud using $T_1$-$T_2$ correlation spectra measurements is generally shown. Initially, at block 20 of FIG. 1A, a sample of drilling mud is collected, placed in an NMR compatible vial and inserted in an NMR system for analysis. A conventional NMR spectrometer with a radio frequency coil and magnet with a homogeneous or nonhomogeneous field can be used. For diffusion measurements, the ability to apply a pulsed magnetic field gradient or a fixed magnetic field gradient in addition to the main magnetic field is preferred.

In an alternative embodiment, drilling fluid can be pumped into a pipe that is contained in a nuclear magnetic resonance spectrometer magnet and radio frequency coil at block 20. The flow is stopped and the 1-D or 2-D nuclear magnetic resonance procedures can be used to measure the oil and water volume percent of the fluid.

Analysis of the sample of drilling mud acquired at block 20 begins with the acquisition of a two dimensional data set for $T_1$-$T_2$ correlation spectra measurements at block 30. There are a variety of approaches for measuring the spin-lattice ($T_1$) relaxation time distribution of the sample, or the spin-spin ($T_2$) relaxation time distribution of the sample.

The preferred approach is to apply a saturation recovery sequence followed by a refocusing sequence to the sample at block 30 of FIG. 1A. Normal saturation recovery sequences are multiple 90° (i.e. $\pi/2$) pulses with short times between pulses.

The saturation recovery sequence in this embodiment is followed by a refocusing sequence such as a Carr-Purcell-Meiboom-Gill (CPMG) echo train sequence. The CPMG sequence is a 90° pulse followed by a train of 180° (i.e. Tr) pulses generating spin echoes. The CPMG sequence, $$M(\tau) = \sum_i M_0 e^{-\frac{\tau}{T_{2i}}},$$

produces a relatively fast measurement and returns a decaying function that is dependent on the water protons and oil proton signal contributions from the sample.

The acquired data set from block 30 is transformed from a time space to a relaxation component space with a two dimensional inverse transform at block 40. On particularly preferred inverse transform is the inverse Laplace transform. Other pulse sequences that could be utilized are the Carr-Purcell or Hahn echo sequence.

The components produced by the transform that are over or under the detection limits of the applied pulse sequences are eliminated at block 50 of FIG. 1A to improve the accuracy and to refine the data.

At block 60, the transformed data are projected onto a plane perpendicular to the line corresponding to $T_1/T_2=1$ where the projected data form a $T_1/T_2$ spectrum in that plane.

The spectrum is fitted to Gaussian peaks to determine the peak areas at block 70 of FIG. 1B. In one embodiment, this is accomplished using a non-negative least squares fitting.

Oil-water cutoff values can be determined based on the maximum peak intensity of the peaks at block 80. The peak areas at the cutoff value and above the cutoff value are attributed to signal arising from oil. Similarly, the peak areas that are below the cutoff value are attributed to water at block 80. The difference in the oil and water spectral regions can be determined from a sample of the pure oil phase or through fitting to a couple of data points on samples with different oil volume percentages. In the two-dimensional procedure, the line of demarcation between the oil and water phases can be set in a similar manner to the 1-D case. In some muds, the oil and water regions overlap in the 1-D spectra and hence improved accuracy can be obtained by utilizing a 2-D procedure to separate the oil and water phases.

Once the peak areas for oil and for water are designated, the peak areas for water and for oil are summed at block 90 of FIG. 1B. Differences in signal intensity from oil and water can optionally be accounted for with reference to Hydrogen Indexes at block 100.

Finally, at block 110, the oil and water ratios by volume are determined from the peak areas and differences in signal intensity.

The technology described herein may be better understood with reference to the accompanying examples, which are intended for purposes of illustration only and should not be construed as in any sense limiting the scope of the technology described herein as defined in the claims appended hereto.

Example 1

In order to demonstrate the technology, analysis of different samples of drilling mud with a range of water and oil percentages was conducted. Water cut measurements were performed on the well blended samples that were loaded into small vials. The range of water cut of interest is 10%-30%. A mud with 28.57% water cut was used as the base mud. Different amounts of diesel were added to the base mud to create various samples of mud with different water cut percentages within the range of interest. Water was added to drilling mud samples to increase their water fraction [m/m]. As the water percentage was increased, the ratio of the signals from the transformed data gave a linear response. Based on the water added, the original water content could also be determined.

The first method tested for the NMR measurement of watercut of the samples was the one-dimensional NMR method. The one-dimensional method only used with drilling muds that show a distinctive separation of water and oil peaks in their $T_1$ or $T_2$ relaxation spectrum. If there is an overlap between the oil and water peaks, then the two dimensional method should be utilized as shown in Example 2.

Drilling mud was placed in the NMR spectrometer in a static setup or pumped to the coil of the spectrometer in a flow setup. The sample was measured using a CPMG (Carr-Purcell-Meiboom-Gill) sequence with optimized parameters. The obtained CPMG data was processed into a $T_2$ relaxation spectrum using an inverse Laplace transformation. In the $T_2$ relaxation spectrum, peaks over and under the detection limit were removed. Peak areas were calculated by fitting the spectrum to Gaussian peaks. A $T_2$ cutoff value was chosen to separate the oil and water peaks. The cutoff value should be bigger than the $T_2$ relaxation times of oil and smaller than the $T_2$ relaxation time of water. The area of the peaks, which have $T_2$ equal to or less than the cutoff value, was attributed to signal from oil, and the area of the peaks with $T_2$ larger than the cutoff value was attributed to signal from water. The volume fractions of oil and water were calculated by dividing the signal of oil and water by the hydrogen indexes of oil and water, respectively. The oil and water ratio (by volume) was then determined from the volume fraction of oil and water.

Example 2

Figure 2A:
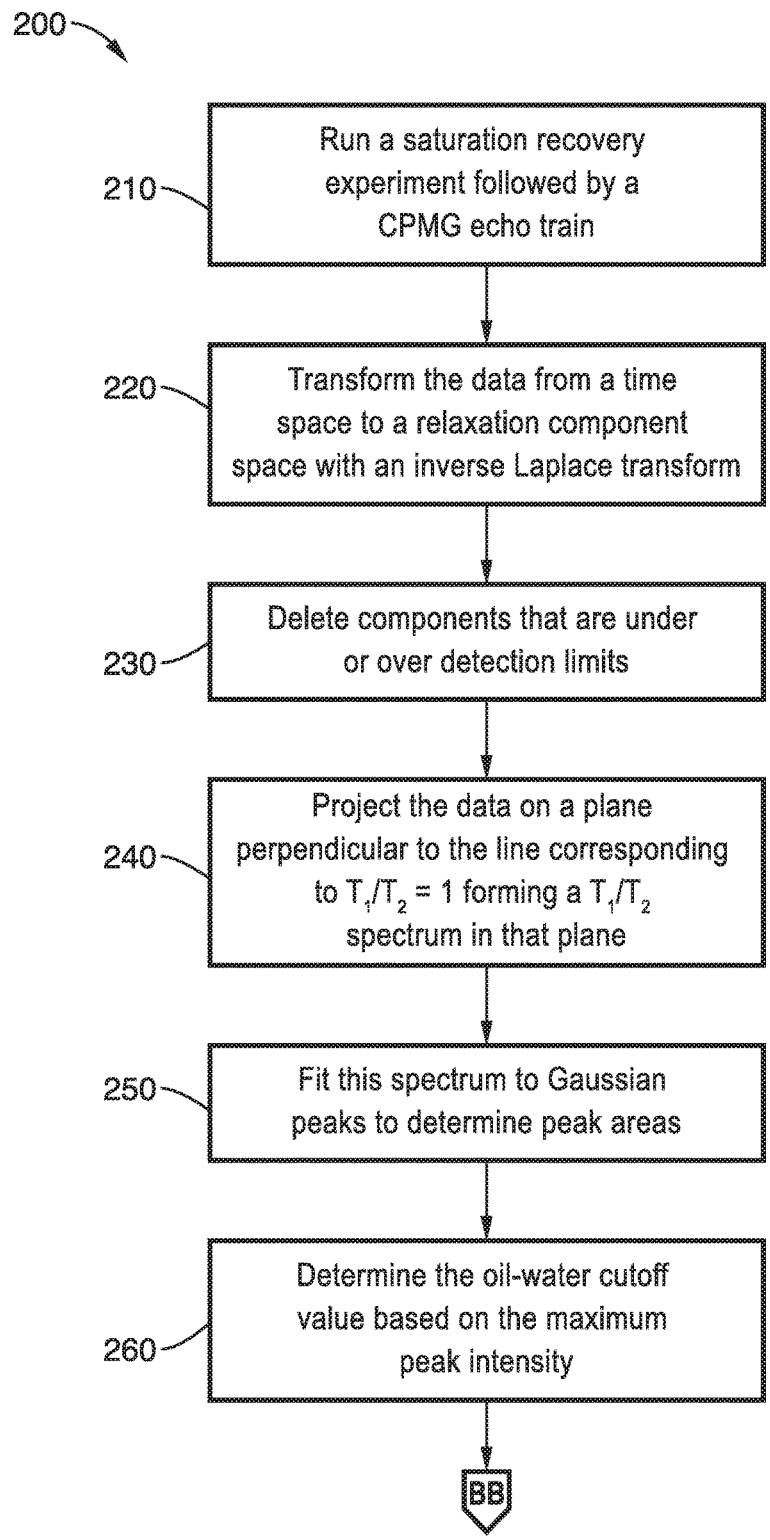
FIG. 2A-FIG. 2B depict a schematic flow diagram of a method of estimating oil-water ratios using NMR signals separated out into two-dimensional relaxation space according to a second embodiment illustrating the technology.
Figure 2B:
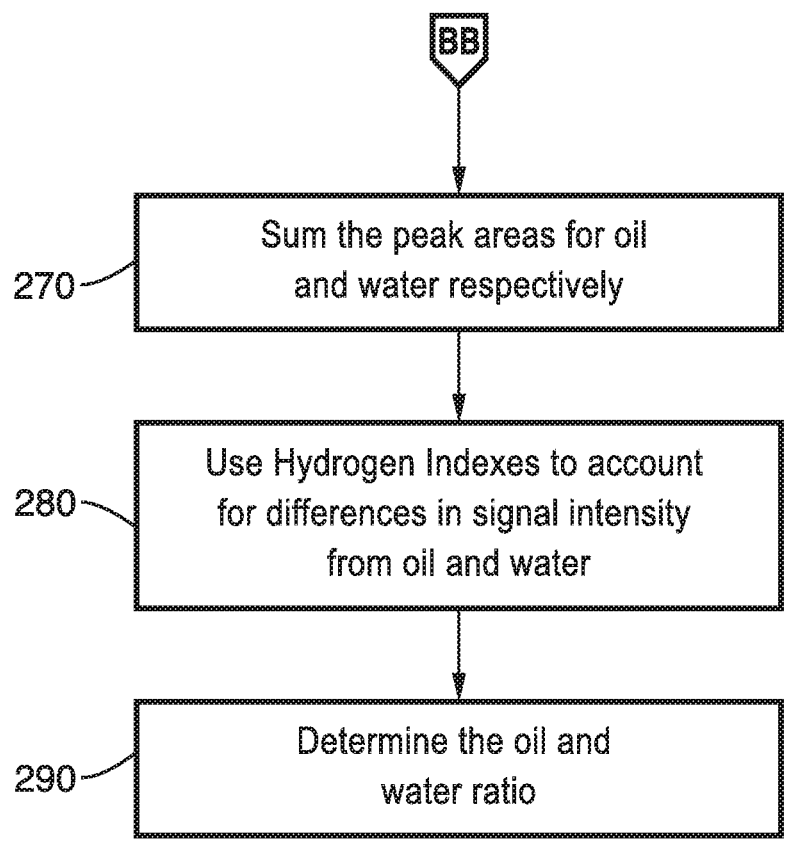

To further demonstrate the operational principles of the methods, a variety of drilling muds with differing oil and water contents were analyzed using a two-dimensional method. Referring now to FIG. 2A and FIG. 2B, an illustration of the method 200 using a two-dimensional approach is shown schematically. Drilling mud was placed in the NMR spectrometer or pumped to the coil of the spectrometer in a flow setup. The sample was measured using a saturation recovery sequence followed by a CPMG echo train with optimized parameters at block 210 of FIG. 2A.

The saturation recovery pulse sequence was used to record the $T_1$ relaxation behavior, and the CPMG sequence was used to capture the $T_2$ relaxation behavior for each of the delay or repetition times in the saturation recovery pulse sequence.

The $T_1$-$T_2$ relaxation data was transformed at block 220 to a two dimensional $T_1$-$T_2$ correlation spectrum using a two dimensional inverse Laplace transformation. The components that were observed to be under or over detection limits were eliminated at block 230.

The spectrum was projected on to a plane that was perpendicular to the line where $T_1=T_2$ at block 240. As a result, the two dimensional spectrum was transformed into a one dimension $T_1/T_2$ spectrum. The one dimensional $T_1/T_2$ spectrum was then fitted to Gaussian peaks to calculate peak areas at block 250.

The cutoff value was determined at block 260 by searching for the best separation point between oil and water peaks. Peak areas above or equal to the cutoff represented the signal from the oil and the peak areas below the cutoff represented signal from water.

The peak areas for water and oil were then summed at block 270 of FIG. 2B to quantify the signal from oil and water, respectively. The volume fractions of oil and water were calculated by dividing the signal of oil and water by the Hydrogen Indexes of oil and water, respectively at block 280. The oil and water ratio (by volume) was then determined from the volume fraction of oil and water at block 290.

The NMR measurements of various samples were compared with the oil volume and water volume from retort measurements. When appropriate, threshold values were used and the measurement error was no more than 1.5%.

From the discussion above it will be appreciated that the technology described herein can be embodied in various ways, including the following:

1. A nuclear magnetic resonance (NMR) method for determining oil and water composition in drilling mud, the method comprising: (a) collecting a sample of the drilling mud; (b) placing the sample in an NMR scanner system; (c) measuring a spin-lattice relaxation time distribution of the sample; (d) evaluating distributions of oil and water phases of the drilling fluid for overlapping components; (e) applying a two-dimensional NMR procedure to separate overlapping components when an overlap is found; (f) quantifying relative portions of the proton NMR signal from the oil and water from the signal intensities from oil and water regions of the one-dimensional; and (g) determining a ratio of oil and water from the quantified proton NMR signals.

2. The method of any preceding embodiment, further comprising: measuring a spin-spin relaxation time distribution of the sample; and quantifying relative portions of the proton NMR signal from the oil and water from the signal intensities from oil and water regions of the one-dimensional or the two-dimensional NMR measurements.

3. The method of any preceding embodiment, wherein the spin-lattice relaxation time distribution is measured with at least one saturation recovery sequence.

4. The method of any preceding embodiment, wherein the spin-spin relaxation time distribution of the sample is measured with a Car-Purcell-Meiboom-Gill (CPMG) echo train sequence.

5. The method of any preceding embodiment, wherein the spin-spin relaxation time distribution of the sample is measured with a Hahn echo sequence.

6. The method of any preceding embodiment, wherein the two-dimensional NMR procedure comprises a spin-lattice versus spin-spin procedure.

7. The method of any preceding embodiment, wherein the two-dimensional NMR procedure comprises a spin-spin versus diffusion procedure.

8. The method of any preceding embodiment, wherein the quantifying of NMR signals further comprises: evaluating peak areas for maximum peak intensities; setting an oil-water cut off value threshold based on maximum peak intensities designating oil peak areas and water peak areas; summing water peak areas and oil peak areas; and accounting for differences in signal intensity between oil and water with Hydrogen Indexes.

9. The method of any preceding embodiment, wherein the peak areas are evaluated by fitting a $T_1/T_2$ spectrum to Gaussian peaks.

10. The method of any preceding embodiment, wherein the oil peak areas are designated at a cutoff value and above and attributed to signal from oil; and wherein the water peak areas are designated at below the cutoff value and are attributed to signal from water.

11. A method for determining oil and water composition in drilling mud, the method comprising: (a) placing a sample of drilling mud in a nuclear magnetic resonance spectrometer; (b) acquiring a two dimensional NMR data set for $T_1$-$T_2$ correlation spectra measurements; (c) transforming the data set from a time space to a relaxation component space with a two dimensional inverse Laplace transform; (d) eliminating transformed components that are outside of the detection limits of the applied pulse sequences to refine data; (e) projecting the refined data on a plane perpendicular to the line corresponding to $T_1/T_2$ to form a $T_1/T_2$ spectrum in the plane; (f) determining peak areas by fitting the $T_1/T_2$ spectrum to Gaussian peaks; and (g) determining oil and water ratios from the peak areas.

12. The method of any preceding embodiment, wherein the two-dimensional NMR data set is acquired by applying a saturation recovery sequence followed by a refocusing sequence to the sample.

13. The method of any preceding embodiment, wherein the refocusing sequence comprises a Car-Purcell-Meiboom-Gill (CPMG) echo train sequence.

14. The method of any preceding embodiment, wherein the refocusing sequence comprises a Hahn echo sequence.

15. The method of any preceding embodiment, further comprising: evaluating the peak areas for maximum peak intensities; setting an oil-water cut off value threshold based on the maximum peak intensities designating oil peak areas and water peak areas; summing water peak areas and oil peak areas; accounting for differences in signal intensity between oil and water with Hydrogen Indexes; and determining an oil to water ratio of the drilling mud sample.

16. The method of any preceding embodiment, wherein the oil peak areas are designated at a cutoff value and above and attributed to signal from oil; and wherein the water peak areas are designated at below the cutoff value and are attributed to signal from water.

17. A nuclear magnetic resonance (NMR) method for determining oil and water composition in drilling mud, the method comprising: (a) collecting a sample of the drilling mud; (b) placing the sample in an NMR spectrometer system; (c) measuring the spin-lattice relaxation time distribution of the sample or a spin-spin relaxation time distribution of the sample; (d) applying a spin-lattice versus spin-spin or a spin-spin versus diffusion two-dimensional procedure to separate the components of the drilling fluid; (e) integrating the signal intensities from the oil and water regions of the one-dimensional or two-dimensional NMR measurements to quantify the relative portion of the proton NMR signal from the oil and water; and (f) determining the ratio of oil and water from the proton NMR signals.

18. The method of any preceding embodiment, wherein the spin-lattice relaxation time distribution is measured with at least one saturation recovery sequence.

19. The method of any preceding embodiment, wherein the spin-spin relaxation time distribution of the sample is measured with a Car-Purcell-Meiboom-Gill (CPMG) echo train sequence.

20. The method of any preceding embodiment, wherein the spin-spin relaxation time distribution of the sample is measured with a Hahn echo sequence.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A nuclear magnetic resonance (NMR) method for determining oil and water composition in drilling mud, the method comprising:
    (a) collecting a sample of drilling mud;
    (b) placing the sample in an NMR scanner system and obtaining proton NMR signals from the sample;
    (c) measuring a spin-lattice relaxation time distribution of the sample from the proton NMR signals;
    (d) evaluating distributions of oil and water phases of the spin-lattice relaxation time distribution of the sample for overlapping components;
    (e) applying a two-dimensional NMR procedure to separate overlapping components when an overlap is found;
    (f) quantifying relative portions of the proton NMR signals from oil and water in the sample from the signal intensities from oil and water components; and
    (g) determining a ratio of oil and water from the quantified NMR signals.

2. The method as recited in claim 1, further comprising: measuring a spin-spin relaxation time distribution of the sample; and
    quantifying relative portions of the proton NMR signal from the oil and water from the signal intensities from oil and water components of the one-dimensional measurement or of the two-dimensional NMR measurement.

3. The method as recited in claim 1, wherein said spin-lattice relaxation time distribution is measured with at least one saturation recovery sequence.

4. The method as recited in claim 1, wherein said spin-spin relaxation time distribution of the sample is measured with a Car-Purcell-Meiboom-Gill (CPMG) echo train sequence.

5. The method as recited in claim 1, wherein said spin-spin relaxation time distribution of the sample is measured with a Hahn echo sequence.

6. The method as recited in claim 1, wherein said two-dimensional NMR procedure comprises a spin-lattice versus spin-spin procedure.

7. The method as recited in claim 1, wherein said two-dimensional NMR procedure comprises a spin-spin versus diffusion procedure.

8. The method as recited in claim 1, wherein said quantifying of NMR signals further comprises:
evaluating NMR signal peak areas for maximum peak intensities;
setting an oil-water cut off value threshold based on said maximum peak intensities designating oil peak areas and water peak areas;
summing designated water peak areas and oil peak areas; and
accounting for differences in signal intensity between oil and water with Hydrogen Indexes.

9. The method as recited in claim 8, wherein said NMR signal peak areas are evaluated by fitting a $T_1/T_2$ spectrum to Gaussian peaks.

10. The method as recited in claim 8, wherein said oil peak areas are designated at a cutoff value and above and attributed to a signal from oil; and wherein said water peak areas are designated at below the cutoff value and are attributed to a signal from water.

11. A method for determining oil and water composition in drilling mud, the method comprising:
(a) placing a sample of drilling mud in a nuclear magnetic resonance spectrometer;
(b) acquiring a two-dimensional NMR data set for $T_1$-$T_2$ correlation spectra measurements;
(c) transforming the data set from a time space to a relaxation component space with a two-dimensional inverse Laplace transform;
(d) eliminating transformed components that are outside of the detection limits of the applied pulse sequences to refine data;
(e) projecting the refined data on a plane perpendicular to the line corresponding to $T_1/T_2$ to form a $T_1/T_2$ spectrum in the plane;
(f) determining peak areas by fitting the $T_1/T_2$ spectrum to Gaussian peaks; and
(g) determining oil and water ratios from the peak areas.

12. The method as recited in claim 11, wherein said two-dimensional NMR data set is acquired by applying a saturation recovery sequence followed by a refocusing sequence to the sample.

13. The method as recited in claim 12, wherein said refocusing sequence comprises a Car-Purcell-Meiboom-Gill (CPMG) echo train sequence.

14. The method as recited in claim 12, wherein said refocusing sequence comprises a Hahn echo sequence.

15. The method as recited in claim 11, further comprising:
evaluating said peak areas for maximum peak intensities;
setting an oil-water cut off value threshold based on the maximum peak intensities designating oil peak areas and water peak areas;
summing water peak areas and oil peak areas;
accounting for differences in signal intensity between oil and water with Hydrogen Indexes; and
determining an oil to water ratio of the drilling mud sample.

16. The method as recited in claim 14, wherein said oil peak areas are designated at a cutoff value and above and attributed to a signal from oil; and
wherein said water peak areas are designated at below the cutoff value and are attributed to a signal from water.

17. A nuclear magnetic resonance (NMR) method for determining oil and water composition in drilling mud, the method comprising:
(a) collecting a sample of the drilling mud;
(b) placing the sample in an NMR spectrometer system and obtain one-dimensional or two-dimensional proton NMR measurements;
(c) measuring the spin-lattice relaxation time distribution of the sample or a spin-spin relaxation time distribution of the sample;
(d) applying a spin-lattice versus spin-spin or a spin-spin versus diffusion two-dimensional procedure to separate the components of the drilling fluid;
(e) integrating the signal intensities from the oil and water components of the one-dimensional or two-dimensional NMR measurements to quantify the relative portion of the proton NMR signal from the oil and water; and
(f) determining the ratio of oil and water from the proton NMR signals.

18. The method as recited in claim 17, wherein said spin-lattice relaxation time distribution is measured with at least one saturation recovery sequence.

19. The method as recited in claim 17, wherein said spin-spin relaxation time distribution of the sample is measured with a Car-Purcell-Meiboom-Gill (CPMG) echo train sequence.

20. The method as recited in claim 17, wherein said spin-spin relaxation time distribution of the sample is measured with a Hahn echo sequence.

* * * * *